United States Patent [19]

Izzo

[11] Patent Number: 4,493,713
[45] Date of Patent: Jan. 15, 1985

[54] ADDED FEATURE TO DISPOSABLE DIAPERS

[76] Inventor: Alexander P. Izzo, 10 Printer Ct., Huntington Station, N.Y. 11746

[21] Appl. No.: 400,627

[22] Filed: Jul. 22, 1982

[51] Int. Cl.³ .............................................. A61F 13/16
[52] U.S. Cl. ................................................... 604/385
[58] Field of Search ............... 604/358, 385; 206/363, 206/438, 440

[56] References Cited

U.S. PATENT DOCUMENTS

| | | | |
|---|---|---|---|
| 3,017,990 | 1/1962 | Singerman | 206/440 |
| 3,148,771 | 9/1964 | Miller, Jr. | 206/440 |
| 3,369,545 | 2/1968 | Wanberg | 604/385 |
| 3,731,689 | 5/1973 | Schaar | 604/385 |
| 3,920,019 | 11/1975 | Schaar | 604/385 |
| 3,927,674 | 12/1975 | Schaar | 604/385 |
| 4,085,753 | 4/1978 | Gellert | 604/385 |
| 4,182,336 | 1/1980 | Black | 604/385 |

Primary Examiner—John D. Yasko
Attorney, Agent, or Firm—Richard L. Miller

[57] ABSTRACT

A disposable diaper containing an integral removable bag that provides sanitary storage conditions for the absorbent layer prior to the diaper's use and provides refuge for the soiled diaper by use of a foldover flap that is sealed with a fastening strip.

7 Claims, 3 Drawing Figures

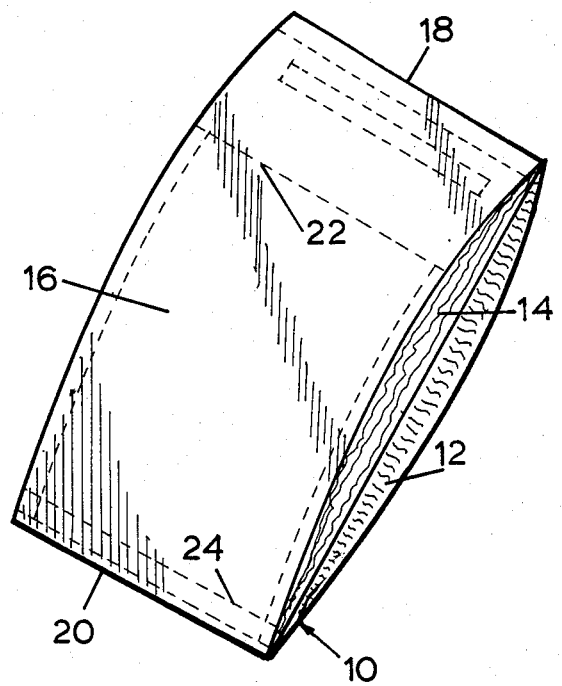
FIG. 1
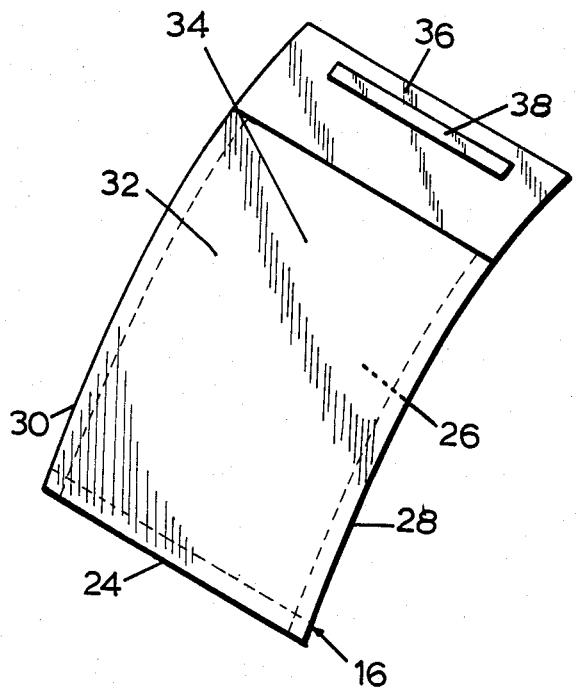
FIG. 2
FIG. 3
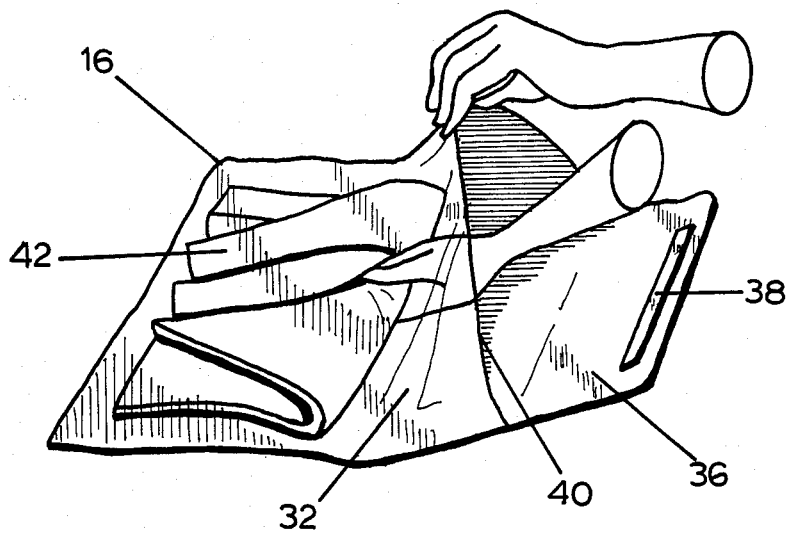

ADDED FEATURE TO DISPOSABLE DIAPERS

BACKGROUND OF THE INVENTION

This invention deals with diapers and more particularly with a disposable diaper utilizing an integral removable bag for discard.

Disposable diapers are preferably provided with an impervious back surface. The back surface of the diaper is the surface opposite the surface of the diaper to be placed against the body. The impervious back surface serves to prevent seepage of liquid collected in the absorbent body of material of the diaper. This eliminates the need for a separate covering garment such as "baby pants", usually employed as a protection against strikethrough in the case of other diapers. Diapers constructed with an impervious back surface are particularly preferred for use at times when washing facilities are not readily accessible or at times of limited storage conditions, for example, when traveling with infants. The impervious backside of the diaper may be a thin plastic sheet which also serves as a reinforcing component of the diaper.

Disposable diapers are suitable for a single use, after which they are discarded. Disposal of the soiled diaper immediately after removal may not be convenient. Furthermore, disposal of the diaper or the fluid absorbent portion of the diaper in flush toilets may not be desirable, in fact, may be prohibited in many instances. The front surface of the diaper (the surface to be placed against the body) usually comprises a fluid pervious sheet covering the absorbent filler material of the diaper. This cover sheet has sufficient wet strength so that it does not disintegrate under use. Because of its wet strength properties it may cause some difficulties in sewage disposal systems, for example, in septic tank systems. It is for this reason that soiled disposable diapers are instead discarded in trash containers until they can be disposed of permanently through other refuse disposal systems. Although stored only temporarily in a trash container, the unsanitary aspect of this is a drawback to the use of disposable diapers.

U.S. Pat. No. 3,731,688 reveals a disposable diaper but makes no mention of an integral removably vehicle for its disposal.

U.S. Pat. No. 4,085,753 reveals a disposable diaper with an integral vehicle for its disposal. However the vehicle is not detachable and is mounted to the backing sheet of the disposable diaper. Additionally, the utilization of this vehicle requires extensive handling of the soiled diaper.

U.S. Pat. No. 3,369,545 reveals a disposable diaper with an integral removable vehicle for its disposal. However, the vehicle does not contain a closing flap with a fastening strip and there is no integral way of sanitary storage.

The present invention utilizes a disposable diaper with an integral removable bag for its disposal. Upon storage of the diaper the removable bag keeps the absorbent bag layer sanitary. Upon use the removable bag is detached and the diaper is placed on the infant. When the infant requires changing a new diaper is procured and its removable bag is detached. The soiled diaper is placed in the bag and the flap is folded over and secured via the fastening strip for sanitary storage until disposed of.

SUMMARY OF THE INVENTION

Accordingly, it is an object of the present invention to provide a disposable diaper.

A further object of the present invention is to provide a disposable diaper having a backing sheet to which an absorbent diaper is attached and having a removable bag covering the absorbent layer and thus keeping it sanitary prior to the diaper's use.

Another object of the pesent invention is to provide a disposable diaper in which the removable bag has perforations at its first end and its second end to allow for its removal for use.

Still a further object of the present invention is to provide a disposable diaper in which the removable bag has a flap at its first end which allows for covering of the removable bag subsequent to its use.

Yet another object of the present invention is to provide a disposable diaper in which the flap contains an attachment strip to seal the flap closed after it is folded over the removable bag.

Still a further object of the present invention is to provide a disposable diaper in which the flap attachment is either loop pile fastener or pressure sensitive adhesive.

Briefly, in accordance with the present invention, there is provided a disposable diaper containing an integral removable bag that provided sanitary storage conditions for the absorbent layer prior to the diaper's use and provides refuge for the soiled diaper by use of a foldover flap that is sealed with either loop pile fastener or pressure sensitive adhesive strip.

Further objects of the invention will appear as the description proceeds.

To the accomplishment of the above and related objects, this invention may be embodied in the form illustrated in the accompanying drawings, attention being called to the fact, however, that the drawings are illustrative only and that changes may be made in the specific construction illustrated and described within the scope of the appended claims.

BRIEF DESCRIPTION OF THE DRAWING FIGURES

The figures in the drawings are briefly described as follows:

FIG. 1 is an isometric projection showing the disposable diaper of the present invention.

FIG. 2 is an isometric projection of the removable bag of the disposable diaper shown in FIG. 1.

FIG. 3 is an isometric projection showing the utilization of the disposable diaper and bag shown in FIG. 1.

In the various figures of the drawing, like reference numbers designate like parts.

DESCRIPTION OF THE PREFERRED EMBODIMENTS

Referring now to FIG. 1, the disposable diaper of the present invention is shown generally at 10 and includes a removable bag at 16. The disposable diaper 10 contains a backing sheet 12 and an absorbent layer 14 which is attached to the backing sheet 12. The removable bag 16 is attached by its first end 18 and its second end 20 to the backing sheet 12 and sandwiches the absorbent layer 14. The removable bag is detachable at its first perforated end 20 and its second perforated end 22.

The removable bag 16 is shown in FIG. 2. The front face 32 is attached to a backing face 26 at its first side 28 and its second side 30 and the second perforated end 24 and thus forming pouch 40. The backing face 26 extends past the front face 32 forming the flap 36. On the flap 36 is a fastening strip 38 such as loop pile fastener or pressure sensitive adhesive, etc. which allows the removable bag 16 to be sealed when the flap 36 is folded over for closing.

In FIG. 3 the removable bag 16 is opened at 40 and a soiled diaper 42 is inserted. The flap 36 will be folded over pouch 32 and sealed by the fastening strip 38. If loop pile fastener is used than naturally the mating pile must be also secured to the bag in its proper respective location generally at 34.

While certain novel features of this invention have been shown and described and are pointed out in the annexed claims, it will be understood that various omissions, substitutions and changes in the forms and details of the device illustrated and in its operation can be made by those skilled in the art with out departing from the spirit of the invention.

What is claimed is:

1. A disposable diaper, comprising: an absorbant layer having opposing sides;
   a backing sheet attached to one side of the absorbant layer; and
   a removable bag having opposing first and second ends, a storage pouch on one surface thereof, and retained onto the opposite side of said absorbant layer so as to cover said absorbant layer and have said absorbant layer sandwiched between said backing sheet and said bag, said bag being attached to said backing sheet by said first and second ends with said pouch facing said absorbant layer, whereby said bag must be separated from the absorbant layer and removed to expose said absorbant layer for application of the diaper onto a person, said bag once removed now being available for disposal into the storage pouch of said bag of a diaper which is now soiled.

2. The disposable diaper as in claim 1, wherein said removable bag is adjacent to said absorbant layer whereby the absorbant layer is kept sanitary by the presence of said bag prior to the diaper's use.

3. The disposable diaper as in claim 2, wherein said removable bag has perforations at said first end and said second end whereby allowing its removal from said backing sheet when it is to be utilized.

4. The disposable diaper as in claim 3, wherein said removable bag has a flap on said first end whereby said removable bag can be covered subsequent to the installation of a soiled diaper.

5. The disposable diaper as in claim 4, wherein said flap of said removable bag contains a means for sealing said flap after it is folded over said pouch.

6. The disposable diaper as in claim 5, wherein said means for sealing is loop pile fastener strip.

7. The disposable diaper as in claim 5, wherein said means for sealing is a pressure sensitive adhesive strip.

* * * * *